(12) United States Patent
Schoenafinger et al.

(10) Patent No.: US 7,049,341 B2
(45) Date of Patent: May 23, 2006

(54) N-BENZOYLUREIDOCINNAMIC ACID DERIVATIVES, PROCESSES FOR PREPARING THEM AND THEIR USE

(75) Inventors: Karl Schoenafinger, Alzenau (DE); Elisabeth Defossa, Idstein (DE); Dieter Kadereit, Idstein (DE); Erich Von Roedern, Hattersheim (DE); Thomas Klabunde, Frankfurt (DE); Hans-Joerg Burger, Morristown, NJ (US); Andreas Herling, Bad Camberg (DE); Karl-Ulrich Wendt, Frankfurt (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 23 days.

(21) Appl. No.: 10/456,570

(22) Filed: Jun. 6, 2003

(65) Prior Publication Data

US 2004/0102518 A1 May 27, 2004

Related U.S. Application Data

(60) Provisional application No. 60/411,982, filed on Sep. 19, 2002.

(30) Foreign Application Priority Data

Jun. 7, 2002 (DE) ................................ 102 25 635

(51) Int. Cl.
*A61K 31/24* (2006.01)
*A61K 31/195* (2006.01)
*C07C 229/00* (2006.01)
*C07C 275/00* (2006.01)

(52) U.S. Cl. ...................... 514/539; 514/563; 514/596; 560/34; 562/439; 564/153

(58) Field of Classification Search ...................... None
See application file for complete search history.

(56) References Cited

U.S. PATENT DOCUMENTS

| | | | |
|---|---|---|---|
| 3,435,116 A | 3/1969 | Weber et al. | |
| 5,190,923 A | 3/1993 | Vincent et al. | |
| 6,221,633 B1 | 4/2001 | Ertl et al. | |
| 6,221,897 B1 | 4/2001 | Frick et al. | |
| 6,245,744 B1 | 6/2001 | Frick et al. | |
| 6,342,512 B1 | 1/2002 | Kirsch et al. | |
| 6,624,185 B1 | 9/2003 | Glombik et al. | |
| 6,884,812 B1 | 4/2005 | Glombik et al. | |

FOREIGN PATENT DOCUMENTS

| | | |
|---|---|---|
| EP | 0193249 | 9/1986 |
| WO | WO 97/26265 | 7/1997 |
| WO | WO 97/41097 | 11/1997 |
| WO | WO 98/08871 | 3/1998 |
| WO | WO 99/03861 | 1/1999 |
| WO | WO 99/15525 | 4/1999 |
| WO | WO 00/40569 | 7/2000 |
| WO | WO 00/63208 | 10/2000 |
| WO | WO 00/64876 | 11/2000 |
| WO | WO 00/64888 | 11/2000 |
| WO | WO 00/66585 | 11/2000 |
| WO | WO 00/71549 | 11/2000 |
| WO | WO 00/78312 | 12/2000 |
| WO | WO 01/09111 | 2/2001 |
| WO | WO 01/83451 | 11/2001 |
| WO | WO 01/85695 | 11/2001 |
| WO | WO 01/91752 | 12/2001 |
| WO | WO 01/94300 | 12/2001 |

OTHER PUBLICATIONS

Asakawa, A., et. al., Cocaine-Amphetamine-Regulated Transcript Influences Energy Metabolism, Anxiety And Gastric Emptying In Mice, Hormone Metabolis Research, (2001), vol. 33, pp. 554-558.
Drueckes, P., et. al., Photmetric Microtiter Assay Of Inorganic Phosphate In The Presence Of Acid-Labile Organic Phosphates, Analytical Biochemistry, (1995), vol. 230, pp. 173-177.
Engers, H.D., et. al., Kinetic Mechanism Of Phosphorylase a. I. Initial Velocity Studies, Journal Of Biochemistry, (1970), vol. 48, pp. 746-754.
Lee, D.W., et. al., Leptin Agonists As A Potential Approach To The Treatment Of Obesity, Drugs Of The Future, (2001), vol. 26, No. 9, pp. 873-881.
Okada, H., et al., Synthesis And Antitumor Of Prodrugs Of Benzoylphenylureas, Chemical And Pharmaceutical Bulletin, (1994), vol. 42, No. 1, pp. 57-61.
Salvador, J., et. al., Perspectives In The Therapeutic Use Of Leptin, Expert Opinion, (2001), vol. 2, No. 10, pp. 1615-1622.
Tyle, P., et. al., Iontophoretic Devices For Drug Delivery, Pharmaceutical Research, (1986), vol. 3, No. 6, pp. 318-326.
Zunfit, H.J.F., et. al., Carob Pulp Preparation For Treatment Of Hypercholesterolemia, Advances In Therapy, (2001), vol. 18, No. 5, pp. 230-236.

*Primary Examiner*—Paul A. Zucker
(74) *Attorney, Agent, or Firm*—Barbara E. Kurys

(57) ABSTRACT

N-Benzoylureidocinnamic acid derivatives, processes for preparing them and their use The invention relates to N-benzoylureidocinnamic acid derivatives and to their physiologically tolerated salts and physiologically functional derivatives. The invention thus relates to compounds of formula I,

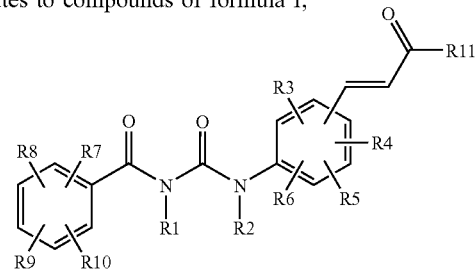

in which the radicals have the given meanings, and to their physiologically tolerated salts and processes for preparing them. The compounds are, for example, suitable for use as antidiabetic agents.

10 Claims, No Drawings

N-BENZOYLUREIDOCINNAMIC ACID DERIVATIVES, PROCESSES FOR PREPARING THEM AND THEIR USE

This application claims the benefit of U.S. Provisional Application No. 60/411,982, filed Sep. 19, 2002 and German Application No. 10225635.7-42 filed Jun. 7, 2002.

DESCRIPTION

N-Benzoylureidocinnamic acid derivatives, processes for preparing them and their use The invention relates to N-benzoylureidocinnamic acid derivatives and to their physiologically tolerated salts and physiologically functional derivatives.

EP 0 193 249 (Duphar) describes acylcarboxyphenylurea derivatives which possess antitumor activity.

The object of the invention is to provide compounds which can be used for preventing and treating type 2 diabetes. In this respect, the compounds should considerably lower the blood sugar level.

The invention therefore relates to compounds of the formula I,

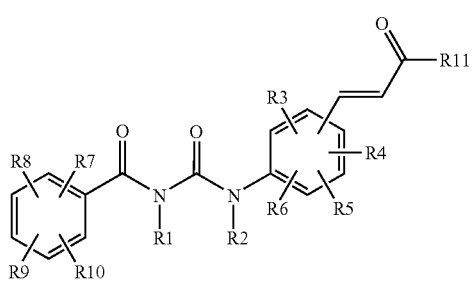

I in which

R7, R8, R9 and R10 are, independently of each other, H, F, Cl, Br, OH, $NO_2$, CN, O—($C_1$–$C_6$)-alkyl, O—($C_2$–$C_6$)-alkenyl, O—($C_2$–$C_6$)-alkynyl, O—$SO_2$—($C_1$–$C_4$)-alkyl, ($C_1$–$C_6$)-alkyl, ($C_2$–$C_6$)-alkenyl or ($C_2$–$C_6$)-alkynyl, wherein the O—($C_1$–$C_6$)-alkyl, O—($C_2$–$C_6$)-alkenyl, O—($C_2$–$C_6$)-alkynyl, O—$SO_2$—($C_1$–$C_4$)-alkyl, ($C_1$–$C_6$)-alkyl, ($C_2$–$C_6$)-alkenyl and ($C_2$–$C_6$)-alkynyl groups can be substituted, more than once, by F, Cl or Br;

R1 and R2 are, independently of each other, H, O—($C_1$–$C_6$)-alkyl, CO—($C_1$–$C_6$)-alkyl, COO—($C_1$–$C_6$)-alkyl, ($C_1$–$C_6$)-alkylene-COOH, ($C_1$–$C_6$)-alkylene-COO—($C_1$–$C_6$)-alkyl or ($C_1$–$C_6$)-alkyl, wherein the ($C_1$–$C_6$)-alkyl group can be substituted by OH, O—($C_1$–$C_4$)-alkyl, $NH_2$, NH($C_1$–$C_4$)-alkyl or N[($C_1$–$C_6$)-alkyl]$_2$;

R3, R4, R5 and R6 are, independently of each other, H, F, Cl, Br, $NO_2$, CN, O—R12, S—R12, COOR12, N(R13)(R14), N(R13)COR15, ($C_1$–$C_6$)-alkyl, ($C_2$–$C_6$)-alkenyl, ($C_2$–$C_6$)-alkynyl, ($C_3$–$C_7$)-cycloalkyl or ($C_3$–$C_7$)-cycloalkyl-($C_1$–$C_4$)-alkylene, wherein the ($C_1$–$C_6$)-alkyl, ($C_2$–$C_6$)-alkenyl, ($C_2$–$C_6$)-alkynyl, ($C_3$–$C_7$)-cycloalkyl and ($C_3$–$C_7$)-cycloalkyl-($C_1$–$C_4$)-alkylene groups can be substituted, more than once, by F, Cl, Br, OR12, COOR12 or N(R16)(R17);

R11 is OR12 or N(R18)(R19);

R12 is H, ($C_1$–$C_8$)-alkyl, ($C_2$–$C_8$)-alkenyl or ($C_2$–$C_8$)-alkynyl, wherein the ($C_1$–$C_8$)-alkyl, ($C_2$–$C_8$)-alkenyl and ($C_2$–$C_8$)-alkynyl groups can be substituted, more than once, by F, Cl, Br, OH or O—($C_1$–$C_4$)-alkyl;

R13 and R14 are, independently of each other, H, ($C_1$–$C_8$)-alkyl, ($C_2$–$C_8$)-alkenyl, ($C_2$–$C_8$)-alkynyl, ($C_3$–$C_7$)-cycloalkyl, ($C_3$–$C_7$)-cycloalkyl-($C_1$–$C_4$)-alkylene, COO—($C_1$–$C_4$)-alkyl, COO—($C_2$–$C_4$)-alkenyl, phenyl or $SO_2$-phenyl, wherein the phenyl ring of the phenyl and $SO_2$-phenyl groups can be substituted, up to two times, by F, Br, Cl, CN, OH, ($C_1$–$C_6$)-alkyl, O—($C_1$–$C_6$)-alkyl, $CF_3$, $OCF_3$, COOH, COO—($C_1$–$C_6$)-alkyl or $CONH_2$;

or the radicals R13 and R14 form, with the nitrogen atom to which they are bonded, a 3-7-membered, saturated heterocyclic ring which can contain up to 2 further heteroatoms from the group N, O or S, wherein the heterocyclic ring can be substituted, up to three times, by F, Cl, Br, OH, Oxo, N(R20)(R21) or ($C_1$–$C_4$)-alkyl;

R16 and R17 are, independently of each other, H, ($C_1$–$C_8$)-alkyl, ($C_2$–$C_8$)-alkenyl, ($C_2$–$C_8$)-alkynyl, ($C_3$–$C_7$)-cycloalkyl, ($C_3$–$C_7$)-cycloalkyl-($C_1$–$C_4$)-alkylene, COO—($C_1$–$C_4$)-alkyl, COO—($C_2$–$C_4$)-alkenyl, phenyl or $SO_2$-phenyl, wherein the phenyl ring of the phenyl and $SO_2$-phenyl groups can be substituted, up to two times, by F, Br, Cl, CN, OH, ($C_1$–$C_6$)-alkyl, O—($C_1$–$C_6$)-alkyl, $CF_3$, $OCF_3$, COOH, COO—($C_1$–$C_6$)-alkyl or $CONH_2$;

or the radicals R16 and R17 form, with the nitrogen atom to which they are bonded, a 3-7-membered, saturated heterocyclic ring which can contain up to 2 further heteroatoms from the group N, O or S, wherein the heterocyclic ring can be substituted, up to three times, by F, Cl, Br, OH, Oxo, N(R20)(R21) or ($C_1$–$C_4$)-alkyl;

R18, R19 are, independently of each other, H, ($C_1$–$C_8$)-alkyl, ($C_2$–$C_8$)-alkenyl, ($C_2$–$C_8$)-alkynyl, ($C_3$–$C_7$)-cycloalkyl, ($C_3$–$C_7$)-cycloalkyl-($C_1$–$C_4$)-alkylene, COO—($C_1$–$C_4$)-alkyl, COO—($C_2$–$C_4$)-alkenyl, phenyl or $SO_2$-phenyl, wherein the phenyl ring of the phenyl and $SO_2$-phenyl groups can be substituted, up to two times, by F, Br, Cl, CN, OH, ($C_1$–$C_6$)-alkyl, O—($C_1$–$C_6$)-alkyl, $CF_3$, $OCF_3$, COOH, COO—($C_1$–$C_6$)-alkyl or $CONH_2$;

or the radicals R18 and R19, together with the nitrogen atom to which they are bonded, form a 3-7-membered, saturated heterocyclic ring which can contain up to 2 further heteroatoms from the group N, O or S, where the heterocyclic ring can be substituted, up to three times, by F, Cl, Br, OH, Oxo, N(R20)(R21) or ($C_1$–$C_4$)-alkyl;

R22 and R23 are, independently of each other, H, ($C_1$–$C_8$)-alkyl, ($C_2$–$C_8$)-alkenyl, ($C_2$–$C_8$)-alkynyl, ($C_3$–$C_7$)-cycloalkyl, ($C_3$–$C_7$)-cycloalkyl-($C_1$–$C_4$)-alkylene, COO—($C_1$–$C_4$)-alkyl, COO—($C_2$–$C_4$)-alkenyl, phenyl or $SO_2$-phenyl, wherein the phenyl ring of the phenyl and $SO_2$-phenyl groups can be substituted up to two times, by F, Br, Cl, CN, OH, ($C_1$–$C_6$)-alkyl, O—($C_1$–$C_6$)-alkyl, $CF_3$, $OCF_3$, COOH, COO—($C_1$–$C_6$)-alkyl or $CONH_2$;

or the radicals R22 and R23, together with the nitrogen atom to which they are bonded, form a 3-7-membered, saturated heterocyclic ring which can contain up to 2 further heteroatoms from the group N, O or S, where the heterocyclic ring can be substituted, up to three times, by F, Cl, Br, OH, Oxo, N(R20)(R21) or ($C_1$–$C_4$)-alkyl;

R15 is ($C_1$–$C_8$)-alkyl, ($C_2$–$C_8$)-alkenyl, ($C_2$–$C_8$)-alkynyl, ($C_3$–$C_7$)-cycloalkyl, ($C_3$–$C_7$)-cycloalkyl-($C_1$–$C_4$)-alkylene, wherein the ($C_1$–$C_8$)-alkyl, ($C_2$–$C_8$)-alkenyl, ($C_2$–$C_8$)-alkynyl, ($C_3$–$C_7$)-cycloalkyl and ($C_3$–$C_7$)-cycloalkyl-($C_1$–$C_4$)-alkylene groups can be substituted more than once by F, $NH_2$, NH($C_1$–$C_4$)-alkyl, N[($C_1$–$C_4$)-alkyl]$_2$, OH, O—($C_1$–$C_4$)-alkyl, O—($C_2$–$C_4$)-alkenyl) or O—CO—($C_1$–$C_4$)-alkyl, COOR12, CON(R13)(R14), heteroaryl, ($C_6$–$C_{10}$)-aryl or ($C_6$–$C_{10}$)-aryl-($C_1$–$C_4$)-alkylene, wherein the heteroaryl, ($C_6$–$C_{10}$)-aryl and ($C_6$–$C_{10}$)-aryl-($C_1$–$C_4$)-alkylene groups can be substituted by O—($C_1$–$C_4$)-alkyl, wherein the O—($C_1$–$C_4$)-alkyl group can be substituted, more than once, by F, Br or Cl;

R20 and R21 are, independently of each other, H, ($C_1$–$C_8$)-alkyl, ($C_2$–$C_8$)-alkenyl, ($C_2$–$C_8$)-alkynyl, ($C_3$–$C_7$)-cycloalkyl, ($C_3$–$C_7$)-cycloalkyl-($C_1$–$C_4$)-alkylene, COO—($C_1$–$C_4$)-alkyl, COO—($C_2$–$C_4$)-alkenyl, phenyl or $SO_2$-phenyl, wherein the phenyl ring of the phenyl and $SO_2$-phenyl groups can be substituted, up to two times, by F, Br, Cl, CN, OH, ($C_1$–$C_6$)-alkyl, O—($C_1$–$C_6$)-alkyl, $CF_3$, $OCF_3$, COOH, COO—($C_1$–$C_6$)-alkyl or $CONH_2$;

and pharmaceutically acceptable salts thereof.

Preferred compounds of the formula I are those in which one or more radicals have the following meaning:

R7, R8, R9 and R10 are, independently of each other, H, F, Cl, Br, OH, $NO_2$, CN, O—($C_1$–$C_6$)-alkyl, O—($C_2$–$C_6$)-alkenyl, O—($C_2$–$C_6$)-alkynyl, O—$SO_2$—($C_1$–$C_4$)-alkyl, ($C_1$–$C_6$)-alkyl, ($C_2$–$C_6$)-alkenyl or ($C_2$–$C_6$)-alkynyl, wherein the O—($C_1$–$C_6$)-alkyl, O—($C_2$–$C_6$)-alkenyl, O—($C_2$–$C_6$)-alkynyl, O—$SO_2$—($C_1$–$C_4$)-alkyl, ($C_1$–$C_6$)-alkyl, ($C_2$–$C_6$)-alkenyl and ($C_2$–$C_6$)-alkynyl groups can be substituted, more than once, by F, Cl or Br;

R1 and R2 are H;

R3, R4, R5 and R6 are, independently of each other, H, F, Cl, Br, $NO_2$, CN, O—R12, S—R12, COOR12, N(R13)(R14), N(R13)COR15, ($C_1$–$C_6$)-alkyl, ($C_2$–$C_6$)-alkenyl, ($C_2$–$C_6$)-alkynyl, ($C_3$–$C_7$)-cycloalkyl or ($C_3$–$C_7$)-cycloalkyl-($C_1$–$C_4$)-alkylene, wherein the ($C_1$–$C_6$)-alkyl, ($C_2$–$C_6$)-alkenyl, ($C_2$–$C_6$)-alkynyl, ($C_3$–$C_7$)-cycloalkyl and ($C_3$–$C_7$)-cycloalkyl-($C_1$–$C_4$)-alkylene groups can be substituted, more than once, by F, Cl, Br, OR12, COOR12 or N(R16)(R17);

R11 is OR12 or N(R18)(R19);

R12 is H, ($C_1$–$C_8$)-alkyl, ($C_2$–$C_8$)-alkenyl or ($C_2$–$C_8$)-alkynyl, wherein the ($C_1$–$C_8$)-alkyl, ($C_2$–$C_8$)-alkenyl and ($C_2$–$C_8$)-alkynyl groups can be substituted, more than once, by F, Cl, Br, OH or O—($C_1$–$C_4$)-alkyl;

R13 and R14 are, independently of each other, H, ($C_1$–$C_8$)-alkyl, ($C_2$–$C_8$)-alkenyl, ($C_2$–$C_8$)-alkynyl, ($C_3$–$C_7$)-cycloalkyl, ($C_3$–$C_7$)-cycloalkyl-($C_1$–$C_4$)-alkylene, COO—($C_1$–$C_4$)-alkyl, COO—($C_2$–$C_4$)-alkenyl, phenyl or $SO_2$-phenyl, wherein the phenyl ring of the phenyl and $SO_2$-phenyl groups can be substituted, up to two times, by F, Br, Cl, CN, OH, ($C_1$–$C_6$)-alkyl, O—($C_1$–$C_6$)-alkyl, $CF_3$, $OCF_3$, COOH, COO—($C_1$–$C_6$)-alkyl or $CONH_2$;

or the radicals R13 and R14 form, with the nitrogen atom to which they are bonded, a 3-7-membered, saturated heterocyclic ring which can contain up to 2 further heteroatoms from the group N, O or S, wherein the heterocyclic ring can be substituted, up to three times, by F, Cl, Br, OH, Oxo, N(R20)(R21) or ($C_1$–$C_4$)-alkyl;

R16 and R17 are, independently of each other, H, ($C_1$–$C_8$)-alkyl, ($C_2$–$C_8$)-alkenyl, ($C_2$–$C_8$)-alkynyl, ($C_3$–$C_7$)-cycloalkyl, ($C_3$–$C_7$)-cycloalkyl-($C_1$–$C_4$)-alkylene, COO—($C_1$–$C_4$)-alkyl, COO—($C_2$–$C_4$)-alkenyl, phenyl or $SO_2$-phenyl, wherein the phenyl ring of the phenyl and $SO_2$-phenyl groups can be substituted, up to two times, by F, Br, Cl, CN, OH, ($C_1$–$C_6$)-alkyl, O—($C_1$–$C_6$)-alkyl, $CF_3$, $OCF_3$, COOH, COO—($C_1$–$C_6$)-alkyl or $CONH_2$;

or the radicals R16 and R17, together with the nitrogen atom to which they are bonded, form a 3-7-membered, saturated heterocyclic ring which can contain up to 2 further heteroatoms from the group N, O or S, wherein the heterocyclic ring can be substituted, up to three times, by F, Cl, Br, OH, Oxo, N(R20)(R21) or ($C_1$–$C_4$)-alkyl;

R18 and R19 are, independently of each other, H, ($C_1$–$C_8$)-alkyl, ($C_2$–$C_8$)-alkenyl, ($C_2$–$C_8$)-alkynyl, ($C_3$–$C_7$)-cycloalkyl, ($C_3$–$C_7$)-cycloalkyl-($C_1$–$C_4$)-alkylene, COO—($C_1$–$C_4$)-alkyl, COO—($C_2$–$C_4$)-alkenyl, phenyl or $SO_2$-phenyl, wherein the phenyl ring of the phenyl and $SO_2$-phenyl groups can be substituted, up to two times, by F, Br, Cl, CN, OH, ($C_1$–$C_6$)-alkyl, O—($C_1$–$C_6$)-alkyl, $CF_3$, $OCF_3$, COOH, COO—($C_1$–$C_6$)-alkyl or $CONH_2$;

or the radicals R18 and R19, together with the nitrogen atom to which they are bonded, form a 3-7-membered, saturated heterocyclic ring which can contain up to 2 further heteroatoms from the group N, O or S, wherein the heterocyclic ring can be substituted, up to three times, by F, Cl, Br, OH, Oxo, N(R20)(R21) or ($C_1$–$C_4$)-alkyl;

R22 and R23 are, independently of each other, H, ($C_1$–$C_8$)-alkyl, ($C_2$–$C_8$)-alkenyl, ($C_2$–$C_8$)-alkynyl, ($C_3$–$C_7$)-cycloalkyl, ($C_3$–$C_7$)-cycloalkyl-($C_1$–$C_4$)-alkylene, COO—($C_1$–$C_4$)-alkyl, COO—($C_2$–$C_4$)-alkenyl, phenyl or $SO_2$-phenyl, wherein the phenyl ring of the phenyl and $SO_2$-phenyl groups can be substituted, up to two times, by F, Br, Cl, CN, OH, ($C_1$–$C_6$)-alkyl, O—($C_1$–$C_6$)-alkyl, $CF_3$, $OCF_3$, COOH, COO—($C_1$–$C_6$)-alkyl or $CONH_2$;

or the radicals R22 and R23, together with the nitrogen atom to which they are bonded, form a 3-7-membered, saturated heterocyclic ring which can contain up to 2 further heteroatoms from the group N, O or S, wherein the heterocyclic ring can be substituted, up to three times, by F, Cl, Br, OH, Oxo, N(R20)(R21) or ($C_1$–$C_4$)-alkyl;

R15 is ($C_1$–$C_8$)-alkyl, ($C_2$–$C_8$)-alkenyl, ($C_2$–$C_8$)-alkynyl, ($C_3$–$C_7$)-cycloalkyl or ($C_3$–$C_7$)-cycloalkyl-($C_1$–$C_4$)-alkylene, wherein the ($C_1$–$C_8$)-alkyl, ($C_2$–$C_8$)-alkenyl, ($C_2$–$C_8$)-alkynyl, ($C_3$–$C_7$)-cycloalkyl and ($C_3$–$C_7$)-cycloalkyl-($C_1$–$C_4$)-alkylene groups can be substituted more than once by F, $NH_2$, NH($C_1$–$C_4$)-alkyl, N[($C_1$–$C_4$)-alkyl]$_2$, OH, O—($C_1$–$C_4$)-alkyl, O—($C_2$–$C_4$)-alkenyl) or O—CO($C_1$–$C_4$)-alkyl, COOR12, CON(R13)(R14), heteroaryl, ($C_6$–$C_{10}$)aryl, ($C_6$–$C_{10}$)-aryl-($C_1$–$C_4$)-alkylene, wherein the heteroaryl, ($C_6$–$C_{10}$)-aryl and ($C_6$–$C_{10}$)-aryl-($C_1$–$C_4$)-alkylene groups can be substituted by O—($C_1$–$C_4$)-alkyl, wherein the O—($C_1$–$C_4$)-alkyl group can be substituted, more than once, by F, Br or Cl;

R20 and R21 are, independently of each other, H, ($C_1$–$C_8$)-alkyl, ($C_2$–$C_8$)-alkenyl, ($C_2$–$C_8$)-alkynyl, ($C_3$–$C_7$)-cycloalkyl, ($C_3$–$C_7$)-cycloalkyl-($C_1$–$C_4$)-alkylene, COO—($C_1$–$C_4$)-alkyl, COO—($C_2$–$C_4$)-alkenyl, phenyl or $SO_2$-phenyl, wherein the phenyl ring of the phenyl and $SO_2$-phenyl groups can be substituted, up to two times, by F, Br, Cl, CN, OH, ($C_1$–$C_6$)-alkyl, O—($C_1$–$C_6$)-alkyl, $CF_3$, $OCF_3$, COOH, COO—($C_1$–$C_6$)-alkyl or $CONH_2$;

and pharmaceutically acceptable salts thereof.

Particularly preferred compounds of formula I are those in which one or more radicals have the following meaning:

R7, R8, R9 and R10 are, independently of each other, H, F or Cl;

R1, R2 and R6 are H;

R3, R4, R5 and R6 are, independently of each other, H, Cl, COOH, COO—($C_1$–$C_4$)-alkyl or NHCOR15;

R11 is OR12 or N(R18)(R19);

R12 is H or ($C_1$–$C_4$)-alkyl;

R18, R19 are, independently of each other, H or ($C_1$–$C_4$)-alkyl;

R15 is ($C_1$–$C_4$)-alkyl, wherein alkyl can be substituted by COOH;

and pharmaceutically acceptable salts thereof.

The alkyl radicals in the substituents R1, R2, R3, R4, R5, R6, R7, R8, R9, R10, R11 R12, R13, R14, R15, R16, R17, R18, R19, R20, R21, R22 or R23 can be either straight-chain or branched.

If radicals or substituents can occur more than once in the compounds of the formula I, such as O—R12, they can then all, independently of each other, have the given meanings and be identical or different.

The invention relates to compounds of the formula I, in the form of their racemates, racemic mixtures and pure enantiomers, and to their diastereomers and mixtures thereof.

Because of their higher solubility in water as compared with the starting compounds or basal compounds, pharmaceutically tolerated salts are particularly suitable for medical applications. These salts must possess a pharmaceutically tolerated anion or cation. Suitable pharmaceutically tolerated acid addition salts of the compounds according to the invention are salts of inorganic acids, such as hydrochloric acid, hydrobromic acid, phosphoric acid, metaphosphoric acid, nitric acid and sulfuric acid, and also of organic acids, such as acetic acid, benzenesulfonic acid, benzoic acid, citric acid, ethanesulfonic acid, fumaric acid, gluconic acid, glycolic acid, isethionic acid, lactic acid, lactobionic acid, maleic acid, malic acid, methanesulfonic acid, succinic acid, p-toluenesulfonic acid and tartaric acid. Suitable pharmaceutically tolerated basic salts are ammonium salts, alkali metal salts (such as sodium salts and potassium salts), alkaline earth metal salts (such as magnesium salts and calcium salts), trometamol (2-amino-2-hydroxymethyl-1,3-propanediol), diethanolamine, lysine or ethylenediamine.

Salts which contain an anion which is not pharmaceutically tolerated, such as trifluoroacetate, also belong within the scope of the invention as useful intermediates for preparing or purifying pharmaceutically tolerated salts and/or for use in nontherapeutic, for example in-vitro, applications.

The term "physiologically functional derivative" which is used here denotes any physiologically tolerated derivative of a compound according to the invention of the formula I, e.g. an ester which is able, on being administered to a mammal, such as a human, to form (directly or indirectly) a compound of the formula I or an active metabolite thereof.

The physiologically functional derivatives also include prodrugs of the compounds according to the invention, as described, for example, in H. Okada et al., Chem. Pharm. Bull, 1994, 42, 57–61. Such prodrugs can be metabolized in vivo to give a compound according to the invention. These prodrugs may or may not themselves be active.

The compounds according to the invention can also be present in different polymorphic forms, e.g. as amorphous and crystalline polymorphous forms. All polymorphous forms of the compounds according to the invention belong within the scope of the invention and are another aspect of the invention.

As used herein, the following definitions apply:

"Patient" means a warm blooded animal, such as for example rat, mice, dogs, cats, guinea pigs, and primates such as humans.

"Treat" or "treating" means to alleviate symptoms, eliminate the causation of the symptoms either on a temporary or permanent basis, or to prevent or slow the appearance of symptoms of the named disorder or condition.

"Therapeutically effective amount" means a quantity of the compound which is effective in treating the named disorder or condition.

"Pharmaceutically acceptable carrier" is a non-toxic solvent, dispersant, excipient, adjuvant or other material which is mixed with the active ingredient in order to permit the formation of a pharmaceutical composition, i.e., a dosage form capable of administration to the patient. One example of such a carrier is a pharmaceutically acceptable oil typically used for parenteral administration.

"Pharmaceutically acceptable salts" means either an acid addition salt or a basic addition salt which is compatible with the treatment of patients for the intended use.

"Pharmaceutically acceptable acid addition salt" is any non-toxic organic or inorganic acid addition salt of the base compounds represented by Formula I or any of its intermediates. Illustrative inorganic acids which form suitable salts include hydrochloric, hydrobromic, sulfuric and phosphoric acid and acid metal salts such as sodium monohydrogen orthophosphate and potassium hydrogen sulfate. Illustrative organic acids which form suitable salts include the mono-, di- and tri-carboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicyclic, 2-phenoxybenzoic, p-toluenesulfonic acid and sulfonic acids such as methanesulfonic acid and 2-hydroxyethanesulfonic acid. Either the mono- or di-acid salts can be formed, and such salts can exist in either a hydrated, solvated or substantially anhydrous form. In general, the acid addition salts of these compounds are more soluble in water and various hydrophilic organic solvents and which in comparison to their free base forms, generally demonstrate higher melting points.

"Pharmaceutically acceptable basic addition salts" means non-toxic organic or inorganic basic addition salts of the compounds of Formula (I) or any of its intermediates. Examples are alkali metal or alkaline-earth metal hydroxides such as sodium, potassium, calcium, magnesium or barium hydroxides; ammonia, and aliphatic, alicyclic, or aromatic organic amines such as methylamine, trimethylamine and picoline. The selection criteria for the appropriate salt will be known to one skilled in the art.

In that which follows, all references to "compound(s) according to formula I" refer to compound(s) of the formula I as described above and to their salts, solvates and physiologically functional derivatives as described herein.

The compound(s) of the formula (I) can also be administered in combination with other active compounds.

The quantity of a compound according to Formula I which is required in order to achieve the desired biological effect depends on a number of factors, e.g. the specific compound which is selected, the intended use, the nature of administration and the clinical condition of the patient. In general, the daily dose is in the range from 0.3 mg to 100 mg (typically from 3 mg to 50 mg) per day per kilogram of bodyweight, e.g. 3–10 mg/kg/day. An intravenous dose can, for example, be in the range from 0.3 mg to 1.0 mg/kg, which dose can expediently be administered as an infusion of from 10 ng to 100 ng per kilogram per minute. Infusion solutions which are suitable for these purposes can, for example, contain from 0.1 ng to 10 mg, typically from 1 ng to 10 mg, per milliliter. Individual doses can, for example, contain from 1 mg to 10 g of the active compound. Thus, ampoules for injections can, for example, contain from 1 mg to 100 mg, and orally administrable individual dose formulations, such as tablets or capsules, can, for example, contain from 1.0 to 1000 mg, typically from 10 to 600 mg. While, for the therapy of the abovementioned conditions, the compounds according to formula I can be used themselves as compounds, they are preferably present, together with a tolerated excipient, in the form of a pharmaceutical composition. The excipient naturally has to be tolerated in the sense that it is compatible with the other components of the composition and is not harmful to the health of the patient.

The excipient can be a solid or a liquid or both and is preferably formulated together with the compound as an individual dose, for example as a tablet, which can contain from 0.05% to 95% by weight of the active compound. Other pharmaceutically active substances can also be present, including other compounds according to formula I. The pharmaceutical compositions according to the invention can be prepared using one of the known pharmaceutical methods, which essentially consist in the constituents being mixed with pharmacologically tolerated excipients and/or auxiliary substances.

Pharmaceutical compositions according to the invention are those which are suitable for oral, rectal, topical, peroral (e.g. sublingual) and parenteral (e.g. subcutaneous, intramuscular, intradermal or intravenous) administration, even though the most suitable mode of administration depends, in each individual case, on the nature and severity of the condition to be treated and on the nature of the compound according to formula I which is employed in each case. Coated formulations and coated delayed-release formulations also belong within the scope of the invention. Preference is given to formulations which are acid-resistant and gastric juice-resistant. Suitable gastric juice-resistant coatings include cellulose acetate phthalate, polyvinyl acetate phthalate, hydroxypropylmethyl cellulose phthalate and anionic polymers of methacrylic acid and methyl methacrylate.

Suitable pharmaceutical compounds for oral administration can be present in separate units, such as capsules, cachets, sucking tablets or tablets which in each case contain a defined quantity of the compound according to formula I; as powders or granules; as a solution or suspension in an aqueous or nonaqueous liquid; or as an oil-in-water or water-in-oil emulsion. As already mentioned, these compositions can be prepared using any suitable pharmaceutical method which comprises a step in which the active compound and the excipient (which can be composed of one or more additional constituents) are brought into contact. In general, the compositions are prepared by uniformly and homogeneously mixing the active compound with a liquid and/or finely divided solid excipient, after which the product is molded, if required. Thus, a tablet, for example, can be prepared by pressing or molding a powder or granulate of the compound, where appropriate together with one or more additional constituents. Pressed tablets can be prepared by tableting the compound in freely flowing form, such as a powder or granulate, where appropriate mixed with a binding agent, lubricant, inert diluent and/or a (several) surface-active/dispersing agent(s) in a suitable machine. Molded tablets can be prepared by molding the pulverulent compound, which is moistened with an inert liquid diluent, in a suitable machine.

Pharmaceutical compositions which are suitable for peroral (sublingual) administration include sucking tablets, which contain a compound according to formula I together with a flavoring agent, usually sucrose and gum arabic or tragacanth, and lozenges, which comprise the compound in an inert base such as gelatin and glycerol or sucrose and gum arabic.

Suitable pharmaceutical compositions for parenteral administration preferably include sterile aqueous preparations of a compound according to formula I which are preferably isotonic with the blood of the intended recipient. These preparations are preferably administered intravenously, even though the administration can also take place as an injection subcutaneously, intramuscularly or intradermally. These preparations can preferably be prepared by mixing the compound with water and making the resulting solution sterile and isotonic with the blood. In general, injectable compositions according to the invention comprise from 0.1 to 5% by weight of the active compound.

Suitable pharmaceutical compositions for rectal administration are preferably present as individual dose suppositories. These can be prepared by mixing a compound according to formula I with one or more conventional solid excipients, for example cocoa butter, and molding the resulting mixture.

Suitable pharmaceutical compositions for topical use on the skin are preferably present as an ointment, cream, lotion, paste, spray, aerosol or oil. Excipients which can be used are vaseline, lanolin, polyethylene glycols, alcohols and combinations of two or more of these substances. The active compound is generally present at a concentration of from 0.1 to 15% by weight of the composition, for example from 0.5 to 2%.

Transdermal administration is also possible. Suitable pharmaceutical compositions for transdermal uses can be present as individual plasters which are suitable for long-term intimate contact with the epidermis of the patient. Such plasters expediently contain the active compound in an aqueous solution, which is, where appropriate, buffered, dissolved and/or dispersed in an adhesive or dispersed in a polymer. A suitable active compound concentration is from approx. 1% to 35%, preferably from approx. 3% to 15%. As a particular possibility, the active compound can, as described, for example, in Pharmaceutical Research, 2(6): 318 (1986), be released by means of electrotransport or iontophoresis.

The following are suitable for use as additional active compounds for the combination preparations:

All antidiabetics which are named in the Rote Liste [Red List] 2001, Chapter 12. They can be combined with the compounds according to the invention of the formula I, particularly for improving the effect synergistically. The active compound combination can be administered either by administering the active compounds separately to the patient or in the form of combination preparations in which several active compounds are present in one pharmaceutical preparation. Most of the active compounds which are listed below are disclosed in USP Dictionary of USAN and International Drug Names, US Pharmacopeia, Rockville 2001.

Antidiabetics include insulin and insulin derivatives, such as Lantus® (see www.lantus.com) or HMR 1964, rapidly acting insulins (see U.S. Pat. No. 6,221,633), GLP-1 derivatives, such as those which were disclosed in WO 98/08871 by Novo Nordisk A/S, and hypoglycemic active compounds which are effective orally.

The hypoglycemic active compounds which are effective orally preferably include sulfonylureas, biguanidines, meglitinides, oxadiazolidinediones, thiazolidinediones, glucosidase inhibitors, glucagon antagonists, GLP-1 agonists, calcium channel openers, such as those which were disclosed by Novo Nordisk A/S in WO 97/26265 and WO 99/03861, insulin sensitizers, inhibitors of liver enzymes which are involved in stimulating gluconeogenesis and/or glycogenolysis, modulators of glucose uptake, compounds, such as antihyperlipidemic active compounds and antilipidemic active compounds, which alter fat metabolism, compounds which decrease the intake of foodstuffs, agonists of PPAR and PXR, and active compounds which act on the ATP-dependent potassium channel of the beta cells.

In one embodiment of the invention, the compounds of the formula I are administered in combination with an HMGCoA reductase inhibitor, such as simvastatin, fluvastatin, pravastatin, lovastatin, atorvastatin, cerivastatin or rosuvastatin.

In another embodiment of the invention, the compounds of the formula I are administered in combination with a cholesterol absorption inhibitor, such as ezetimibe, tiqueside or pamaqueside.

In another embodiment of the invention, the compounds of the formula I are administered in combination with a PPAR gamma agonist, such as rosiglitazone, pioglitazone, JTT-501 or GI 262570.

In another embodiment of the invention, the compounds of the formula I are administered in combination with a PPAR alpha agonist, such as GW 9578 or GW 7647.

In another embodiment of the invention, the compounds of the formula I are administered in combination with a mixed PPAR alpha/gamma agonist, such as GW 1536, AVE 8042, AVE 8134 or AVE 0847, or as described in PCT/US00/11833, PCT/US00/11490 or DE10142734.4.

In another embodiment of the invention, the compounds of the formula I are administered in combination with a fibrate, such as fenofibrate, clofibrate or bezafibrate.

In another embodiment of the invention, the compounds of the formula I are administered in combination with an MTP inhibitor, such as implitapide, BMS-201038 or R-103757.

In another embodiment of the invention, the compounds of the formula I are administered in combination with a bile acid absorption inhibitor (see, for example, U.S. Pat. No. 6,245,744 or U.S. Pat. No. 6,221,897), such as HMR 1741.

In another embodiment of the invention, the compounds of the formula I are administered in combination with a CETP inhibitor, such as JTT-705.

In another embodiment of the invention, the compounds of the formula I are administered in combination with a polymeric bile acid adsorber, such as cholestyramine or colesevelam.

In another embodiment of the invention, the compounds of the formula I are administered in combination with an LDL receptor inducer (see U.S. Pat. No. 6,342,512), such as HMR1171 or HMR1586.

In another embodiment of the invention, the compounds of the formula I are administered in combination with an ACAT inhibitor, such as avasimibe.

In another embodiment of the invention, the compounds of the formula I are administered in combination with an antioxidant, such as OPC-14117.

In another embodiment of the invention, the compounds of the formula I are administered in combination with a lipoprotein lipase inhibitor, such as NO-1886.

In another embodiment of the invention, the compounds of the formula I are administered in combination with an ATP citrate lyase inhibitor, such as SB-204990.

In another embodiment of the invention, the compounds of the formula I are administered in combination with a squalene synthetase inhibitor, such as BMS-188494.

In another embodiment of the invention, the compounds of the formula I are administered in combination with a lipoprotein(a) antagonist, such as Cl-1027 or nicotinic acid In another embodiment of the invention, the compounds of the formula I are administered in combination with a lipase inhibitor, such as orlistat.

In another embodiment of the invention, the compounds of the formula I are administered in combination with insulin.

In another embodiment, the compounds of the formula I are administered in combination with a sulfonylurea, such as tolbutamide, glibenclamide, glipizide or glimepiride.

In another embodiment, the compounds of the formula I are administered in combination with a biguanide, such as metformin.

In another embodiment, the compounds of the formula I are administered in combination with a meglitinide, such as repaglinide.

In another embodiment, the compounds of the formula I are administered in combination with a thiazolidinedione, such as troglitazone, ciglitazone, pioglitazone, rosiglitazone or the compounds which are disclosed by Dr. Reddy's Research Foundation in WO 97/41097, in particular 5-[[4-[(3,4-dihydro-3-methyl-4-oxo-2-quinazolinylmethoxy]phenyl]methyl]-2,4-thiazolidinedione.

In another embodiment, the compounds of the formula I are administered in combination with an α-glucosidase inhibitor, such as miglitol or acarbose.

In another embodiment, the compounds of the formula I are administered in combination with an active compound which acts on the ATP-dependent potassium channel of the beta cells, such as tolbutamide, glibenclamide, glipizide, glimepiride or repaglinide.

In another embodiment, the compounds of the formula I are administered in combination with more than one of the abovementioned compounds, for example in combination with a sulfonylurea and mefformin, a sulfonylurea and acarbose, repaglinide and metformin, insulin and a sulfonylurea, insulin and mefformin, insulin and troglitazone, insulin and lovastatin, etc.

In another embodiment, the compounds of the formula I are administered in combination with CART modulators (see "Cocaine-amphetamine-regulated transcript influences energy metabolism, anxiety and gastric emptying in mice" Asakawa, A, et al., M.:Hormone and Metabolic Research (2001), 33(9), 554–558), NPY antagonists, e.g. naphthalene-1-sulfonic acid {4-[(4-aminoquinazolin-2-ylamino)methyl]cyclohexylmethyl}amide hydrochloride (CGP 71683A)), MC4 agonists (e.g. 1-amino-1,2,3,4-tetrahydronaphthalene-2-Carboxylic acid [2-(3a-benzyl-2-methyl-3-oxo-2,3,3a,4,6,7-hexahydropyrazolo[4,3-C]pyridin-5-yl)-1-(4-Chlorophenyl)-2-oxoethyl]amide; (WO 01/91752)), orexin antagonists (e.g. 1-(2-methylbenzoxazol-6-yl)-3-[1,5]naphthyridin-4-ylurea hydrochloride (SB-334867-A)), H3 agonists (3-Cyclohexyl-1-(4,4-dimethyl-1,4,6,7-tetrahydroimidazo[4,5-C]pyridin-5-yl)propan-1-one oxalic acid salt (WO 00/63208)); TNF agonists, CRF antagonists (e.g. [2-methyl-9-(2,4,6-trimethylphenyl)-9H-1,3,9-triazafluoren-4-yl]dipropylamine (WO 00/66585)), CRF BP antagonists (e.g. urocortin), urocortin agonists, β3-agonists (e.g. 1-(4-Chloro-3-methanesulfonylmethylphenyl)-2-[2-(2,3-dimethyl-1H-indol-6-yloxy)ethylamino]ethanol hydrochloride (WO 01/83451)), MSH (melanocyte-stimulating hormone) agonists, CCK-A agonists (e.g. {2-[4-(4-Chloro-2,5-dimethoxyphenyl)-5-(2-Cyclohexylethyl)thiazol-2-ylcarbamoyl]-5,7-dimethylindol-1-yl}acetic acid trifluoroacetic acid salt (WO 99/15525)); serotonin reuptake inhibitors (e.g. dexfenfluramines), mixed serotonin compounds and noradrenergic compounds (e.g. WO 00/71549), 5HT agonists, e.g. 1-(3-ethylbenzofuran-7-yl)piperazine oxalic acid salt (WO 01/09111), bombesin agonists, galanin antagonists, growth hormone (e.g. human growth hormone), growth hormone-releasing compounds (tert-butyl 6-benzyloxy-1-(2-diisopropylaminoethylcarbamoyl)-3,4-dihydro-1H-isoquinoline-2-Carboxylate (WO 01/85695)), TRH agonists (see, for example, EP 0 462 884) uncoupling protein 2- or 3-modulators, leptin agonists (see, for example, Lee, Daniel W.; Leinung, Matthew C.; Rozhavskaya-Arena, Marina; Grasso, Patricia. Leptin agonists as a potential approach to the treatment of obesity. Drugs of the Future (2001), 26(9), 873–881), DA agonists (bromocriptine, doprexin), lipase/ amylase inhibitors (e.g. WO 00/40569), PPAR modulators (e.g. WO 00/78312), RXR modulators or TR β-agonists.

In another embodiment of the invention, the additional active compound is leptin; see, e.g., "Perspectives in the therapeutic use of leptin", Salvador, Javier; Gomez-Ambrosi, Javier; Fruhbeck, Gema, Expert Opinion on Pharmacotherapy (2001), 2(10), 1615–1622.

In another embodiment, the additional active compound is dexamphetamine or amphetamine.

In another embodiment, the additional active compound is flenfluramine or dexfenfluramine.

In another embodiment, the additional active compound is sibutramine.

In another embodiment, the additional active compound is orlistat.

In another embodiment, the additional active compound is mazindol or phentermine.

In another embodiment, the compounds of the formula I are administered in combination with bulk materials, preferably insoluble bulk materials (see, e.g., Carob/Caromax® (Zunft H J; et al., Carob pulp preparation for treatment of hypercholesterolemia, ADVANCES IN THERAPY (2001 Sep-Oct), 18(5), 230–6), Caromax is a carob-containing product from Nutrinova, Nutrition Specialties & Food Ingredients GmbH, Industriepark Hochst, 65926 Frankfurt/Main)). The combination with Caromax® can be effected in one preparation or by administering compounds of the formula I and Caromax® separately. In this connection, Caromax® can also be administered in the form of foodstuffs, such as in bakery products or muesli bars.

It will be understood that each suitable combination of the compounds according to the invention with one or more of the above-mentioned compounds and, as desired, one or more further pharmacologically active substances, is regarded as coming within the protective scope of the present invention.

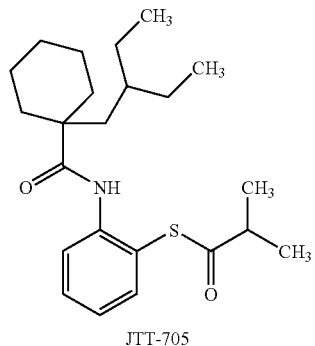

JTT-705

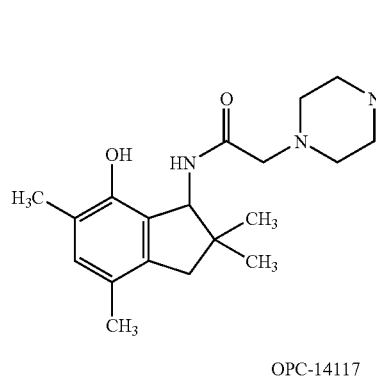

OPC-14117

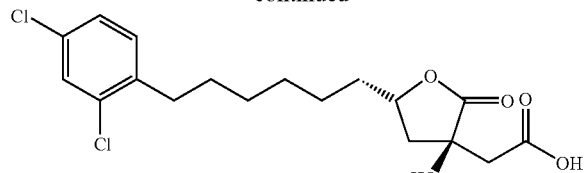

SB-204990

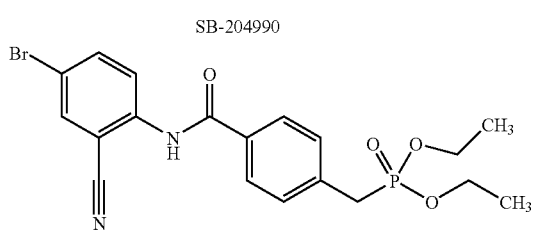

NO-1886

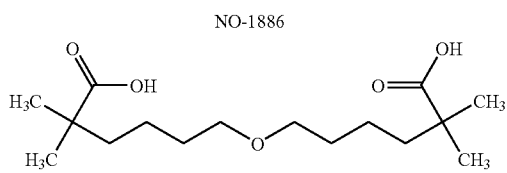

CI-1027

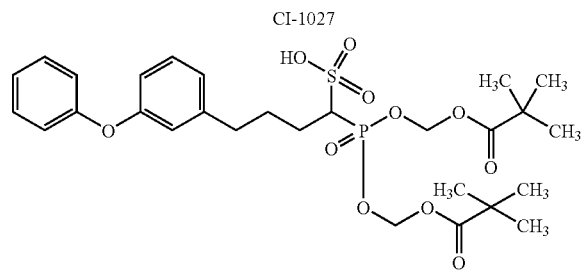

BMS-188494

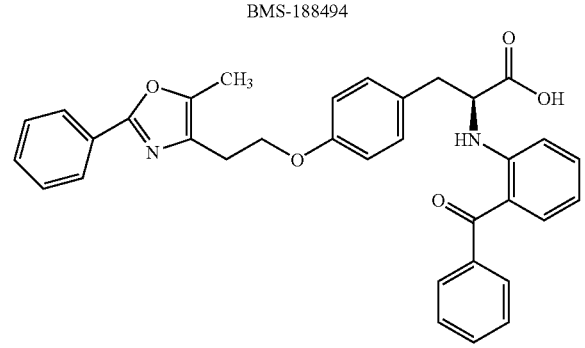

GI 262570

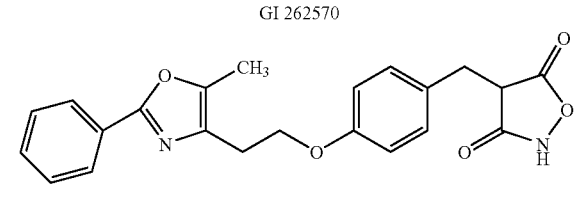

JTT-501

All references cited herein are hereby incorporated in their entirety by reference.

The above disclosure generally describes the present invention. A more complete understanding can be obtained by reference to the following specific examples which are provided herein for purposes of illustration only, and are not intended to limit the scope of the invention.

TABLE 1

Examples of the formula I

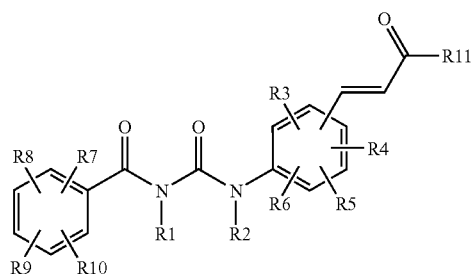

| Ex. | R7, R8, R9, R10 | R1 | R2 | R3 | R4 | R5 | R6 | Connection | R11 | MS* |
|---|---|---|---|---|---|---|---|---|---|---|
| 1 | 4-Cl, 2-F, H, H | H | H | H | H | H | H | C-2 | OH | ok |
| 2 | 2-Cl, 4-F, 5-F, H | H | H | H | H | H | H | C-2 | OH | ok |
| 3 | 2-Cl, 4-F, 5-F, H | H | H | 3-H | 4-H | 5-NHCOCH$_3$ | 6-H | C-2 | OH | ok |
| 4 | 2-Cl, 4-F, 5-F, H | H | H | 3-H | 4-H | 5-NHCOCOOH | 6-H | C-2 | OH | ok |
| 5 | 2-Cl, 4-F, 5-F, H | H | H | 3-H | 4-H | 5-NHCOCH$_2$COOH | 6-H | C-2 | OH | ok |
| 6 | 2-Cl, 4-F, 5-F, H | H | H | 3-H | 4-H | 5-NHCO(CH$_2$)$_2$COOH | 6-H | C-2 | OH | ok |
| 7 | 2-Cl, 4-F, 5-F, H | H | H | 3-H | 4-COOH | 5-H | 6-H | C-2 | OH | ok |
| 8 | 2-Cl, 4-F, 5-F, H | H | H | 2-Cl | 3-H | 4-H | 6-H | C-5 | OH | ok |
| 9 | 4-Cl, 2-F, H, H | H | H | 2-Cl | 3-H | 4-H | 6-H | C-5 | OH | ok |
| 10 | 2-Cl, 4-F, 5-F, H | H | H | 3-H | 4-H | 5-H | 6-H | C-2 | OCH$_3$ | ok |
| 11 | 2-Cl, 4-F, 5-F, H | H | H | 3-H | 4-COOCH$_3$ | 5-H | 6-H | C-2 | OCH$_3$ | ok |
| 12 | 2-Cl, 4-F, 5-F, H | H | H | 3-H | 4-COOH | 5-H | 6-H | C-2 | OCH$_3$ | ok |
| 13 | 2-Cl, 4-F, 5-F, H | H | H | H | H | H | H | C-2 | N(CH$_3$)$_2$ | ok |
| 14 | 2-Cl, 4-F, 5-F, H | H | H | H | H | H | H | C-2 | NH$_2$ | ok |

*The information "MS is Ok" is understood as meaning that a mass spectrum or HPLC/MS was measured and the molar peak (molar mass + H$^+$) was detected in this spectrum.

The compounds of the formula I are characterized by advantageous effects on sugar metabolism; in particular, they lower the blood sugar level and are suitable for treating type 2 diabetes. The compounds can therefore be used on their own or in combination with other blood sugar-lowering active compounds (antidiabetics).

The compounds of formula I are furthermore suitable for treating late damage in diabetes, such as nephropathy, retinopathy, neuropathy and cardiac infarction, myocardial infarction, peripheral arterial occlusion diseases, thromboses, arteriosclerosis, syndrome X, obesity, inflammations, immune diseases, autoimmune diseases, such as AIDS, asthma, osteoporosis, cancer, psoriasis, Alzheimer's disease, schizophrenia and infectious diseases.

The activity of the compounds was tested as follows:

Glycogen Phosphorylase a Activity Test

The effect of compounds on the activity of the active form of glycogen phosphorylase (GPa) was measured in the reverse direction by monitoring the synthesis of glycogen from glucose 1-phosphate by determining the release of inorganic phosphate. All the reactions were carried out as duplicate determinations in 96-well microtiter plates (Half Area Plates, Costar No. 3696), with the change in absorption due to the formation of the reaction product being measured, at the wavelength specified below, in a Multiscan Ascent Elisa Reader (Lab Systems, Finland). In order to measure the enzymic activity of GPa in the reverse direction, the conversion of glucose 1-phosphate into glycogen and inorganic phosphate was measured in accordance with the general method of Engers et al. (Engers H D, Shechosky S, Madsen N B, Can J Biochem 1970 July;48(7): 746–754) but with the following modifications: Human glycogen phosphorylase a (for example containing 0.76 mg of protein/ml (Aventis Pharma Deutschland GmbH), dissolved in buffer solution E (25 mM β-glycerophosphate, pH 7.0, 1 mM EDTA and 1 mM dithiothreitol), was diluted with buffer T (50 mM Hepes, pH 7.0, 100 mM KCl, 2.5 mM EDTA, 2.5 mM MgCl$_2$.6H$_2$O), and addition of 5 mg of glycogen/ml, to a concentration of 10 μg of protein/ml. Test substances were prepared as a 10 mM solution in DMSO and diluted down to 50 μM with buffer solution T. 10 μl of 37.5 mM glucose, dissolved in buffer solution T and 5 mg/ml of glycogen, and also 10 μl of a solution of human glycogen phosphorylase a (10 μg of protein/ml) and 20 μl of glucose 1-phosphate, 2.5 mM, were added to 10 ml of the solution. The basal value of the activity of the glycogen phosphorylase a in the absence of test substance was determined by adding 10 μl of buffer solution T (0.1% DMSO). The mixture was incubated at room temperature for 40 minutes and the inorganic phosphate which was released was measured using the general method of Drueckes et al. (Drueckes P, Schinzel R, Palm D, Anal Biochem 1995 Sep. 1;230(1):173–177) but with the following modifications: 50 μl of a stop solution of 7.3 mM ammonium molybdate, 10.9 mM zinc acetate, 3.6% ascorbic acid, 0.9% SDS are added to 50 μl of the enzyme mixture. After 60 minutes of incubation at 45° C., the absorption was measured at 820 nm. In order to determine the background absorption, the stop solution was added immediately after adding the glucose 1-phosphate solution in a separate assay. This test was carried out using a 10 μM concentration of the test substance in order to determine the respective inhibition of glycogen phosphorylase a by the test substance in vitro.

TABLE 2

| Ex. | Biological activity % inhibition at 10 μM |
|---|---|
| 1 | 100 |
| 2 | 101 |
| 3 | 95 |
| 4 | 95 |
| 5 | 96 |
| 6 | 92 |
| 7 | 96 |
| 8 | 96 |
| 9 | 84 |
| 10 | 83 |
| 11 | 91 |
| 12 | 104 |
| 13 | 91 |
| 14 | 90 |

It can be seen from the table that the compounds of the formula I inhibit the activity of glycogen phosphorylase a and are therefore well suited for lowering the blood sugar level. They are thus particularly suitable for the prevention and treatment of type 2 diabetes.

The preparation of some examples is described in detail below. The remaining compounds of formula I were obtained in an analogous manner:

EXAMPLE 2

3-{2-[3-(2-chloro-4,5-difluorobenzoyl)ureido]phenyl}acrylic acid a) 2-chloro-4,5-difluorobenzoyl isocyanate 2-chloro-4,5-difluorobenzamide was dissolved in dichloromethane, after which 1.5 eq. of oxalyl chloride were added and the reaction mixture was heated to reflux for 16 hours. The reaction mixture was then concentrated under high vacuum and used in step b without any further purification.

b) 3-{2-[3-(2-chloro-4,5-difluorobenzoyl)ureido]phenyl}acrylic acid 0.76 g (3.5 mmol) of 2-chloro-4,5-difluorobenzoyl isocyanate from step a in 6 ml of acetonitrile were added to 0.41 g (2.5 mmol) of 3-(2-aminophenyl)acrylic acid and the mixture was reacted for 2 hours at 40° C. After the mixture has cooled down to room temperature, the precipitate is filtered off with suction, washed twice with acetonitrile, sucked dry and dried. 0.72 g (76%) of the desired product is obtained.

m.p.: 188.5, decomposition

Examples 1, 8, 9 and 10 were prepared from the corresponding aminoacrylic acids and the corresponding isocyanates in analogy with Example 2.

EXAMPLE 3

3-{4-Acetylamino-2-[3-(2-chloro-4,5-difluorobenzoyl)ureido]phenyl}acrylic acid a) Methyl 3-{2-[3-(2-chloro-4,5-difluorobenzoyl)ureido]-4-nitrophenyl}-acrylate 1.0 g (4.5 mmol) of methyl 3-(2-amino-4-nitrophenyl)acrylate (prepared by nitrating methyl 3-(2-aminophenyl)acrylate with urea nitrate in conc. sulfuric acid) were reacted with 0.98 g (4.5 mmol) of 2-chloro-4,5-difluorobenzoyl isocyanate (example 2a) in 6 ml of acetonitrile, and the reaction mixture was stirred at room temperature for 30 minutes. The precipitate was filtered off with suction, washed with diethyl ether and dried. 1.9 g (96%) of the desired product were obtained.

b) Methyl 3-{4-amino-2-[3-(2-chloro-4,5-difluorobenzoyl)ureido]phenyl}-acrylate 1.9 g (4.3 mmol) of methyl 3-{2-[3-(2-chloro-4,5-difluorobenzoyl)ureido]4-nitrophenyl}acrylate were heated to boiling temperature in 100 ml of ethyl acetate and 4.86 g (21.6 mmol) of SnCl$_2$ monohydrate were then added. After an hour, the mixture was allowed to cool down to room temperature and adjusted to pH 8 using a 10% solution of sodium hydrogen carbonate. The resulting precipitate was filtered off with suction and washed with methanol. The organic phase was washed twice with H$_2$O, dried and concentrated in vacuo. The resulting product was used in step c without any further purification.

c) Methyl 3-{4-acetylamino-2-[3-(2-chloro-4,5-difluorobenzoyl)ureido]phenyl}acrylate 6 ml of N-methylpyrrolidone, 1.11 g (3.4 mmol) of cesium carbonate and 0.27 g (3.4 mmol) of acetyl chloride were added to 0.70 g (1.7 mmol) of methyl 3-{4-amino-2-[3-(2-chloro-4,5-difluorobenzoyl)ureido]phenyl}acrylate and the mixture was stirred at room temperature for 30 minutes. It was then diluted with H$_2$O and extracted with ethyl acetate. The organic phase was washed with H$_2$O, dried and concentrated. 0.65 g (85%) of the desired product was obtained.

d) 3-{4-Acetylamino-2-[3-(2-chloro-4,5-difluorobenzoyl)ureido]phenyl}-acrylic acid 0.65 g (1.4 mmol) of methyl 3-{4-acetylamino-2-[3-(2-chloro-4,5-difluorobenzoyl)ureido]phenyl}acrylate was dissolved in 8 ml of tetrahydrofuran, and 8 ml of H$_2$O and 0.17 g (7.2 mmol) of lithium hydroxide were added. After 15 hours at room temperature, the mixture was made acid with 2 N hydrochloric acid and extracted with ethyl acetate. The organic phase was dried, concentrated and stirred up with diethyl ether. The resulting precipitate was filtered off with suction and yielded 77 mg (13%) of the desired product.

M.p.: 196° C., decomposition

EXAMPLE 7

4-[3-(2-chloro-4,5-difluorobenzoyl)ureido]-3-(2-methoxycarbonylvinyl)benzoic acid 0.22 g (0.5 mmol) of methyl 4-[3-(2-chloro-4,5-difluorobenzoyl)ureido]-3-(2-methoxycarbonylvinyl)benzoate (example 11 c) were dissolved in 10 ml of THF, after which 10 ml of H$_2$O and 0.06 g (2.4 mmol) of lithium hydroxide were added. After 2 hours, the mixture was made acid with 2 N hydrochloric acid; this was then followed by extraction with ethyl acetate and concentration. Following preparative HPLC (column: Waters Xterra ™MS C$_{18}$, 5 μm, 30×100 mm, mobile phase: A: H$_2$O+0.2% trifluoroacetic acid, B: acetonitrile, gradient: 2.5 minutes 90% A/10% B to 17.5 minutes 10% A/90% B), 0.02 g (10%) of the desired product was obtained.

M.p.: 99° C.

17

EXAMPLE 11

Methyl 4-[3-(2-chloro-4,5-difluorobenzoyl)ureido]-3-(2-methoxycarbonylvinyl)benzoate a) Methyl 4-amino-3-iodobenzoate 10.4 g (68.8 mmol) of methyl 4-aminobenzoate were dissolved in 100 ml of acetic acid and 11.17 g (68.8 mmol) of iodine monochloride in 100 ml of acetic acid were added. In connection with this, the reaction temperature rose to 30° C. After an hour at room temperature, the mixture was poured onto a 10% solution of sodium hydrogen carbonate and the whole was extracted with dichloromethane; the organic phase was dried and concentrated. 14 g (73%) of the desired product were obtained.

b) Methyl 4-amino-3-(2-methoxycarbonylvinyl)benzoate 0.5 g (1.8 mmol) of methyl 4-amino-3-iodobenzoate, 1.1 eq. of methyl acrylate, 2.5 eq. of cesium carbonate, 1 eq. of ("Bu)$_4$NHSO$_4$, 0.1 eq. of triphenyl phosphine, 0.1 eq. of palladium acetate, 2 ml of acetonitrile and 2 ml of H$_2$O were heated, for 5 minutes under an argon atmosphere, in a microwave at 120° C. and 140 watts. Ethyl acetate was added to the eaction mixture and the whole was washed with H$_2$O, dried and oncentrated. This resulted in 0.3 g (71%) of the desired product, which as reacted in step c without any further purification.

c) Methyl 4-[3-(2-chloro-4,5-difluorobenzoyl)ureido]-3-(2-methoxycarbonylvinyl)benzoate Methyl 4-amino-3-(2-methoxycarbonylvinyl)benzoate was prepared from methyl 4-amino-3-(2-methoxycarbonylvinyl)benzoate and 2-chloro-4,5-difluorobenzoyl isocyanate in analogy with example 3a.

M.p.: 183° C.

EXAMPLE 12 a) 4-Amino-3-iodobenzoic acid 1.73 g (43.4 mmol) of sodium hydroxide in 100 ml of methanol and 100 ml of H$_2$O were added to 6.0 g (21.7 mmol) of methyl 4-amino-3-iodobenzoate and the mixture was stirred at room temperature for 16 hours. It was made to pH 9 with 2 N hydrochloric acid and extracted with ethyl acetate. The organic phase was dried and concentrated. 5.1 g (89%) of the desired product were obtained.

b) 4-Amino-3-(2-methoxycarbonylvinyl)benzoic acid 0.5 g (1.9 mmol) of 4-amino-3-iodobenzoic acid, 0.18 g (2.1 mmol) of methyl acrylate, 1.54 g (4.8 mmol) of cesium carbonate, 0.64 g (1.9 mmol) of ("Bu)$_4$NHSO$_4$, 0.05 g (0.2 mmol) of triphenyl phosphine and 0.04 g (0.2 mmol) of palladium acetate, 1.5 ml of acetonitrile and 1.5 ml of H$_2$O were heated, for 5 minutes under an argon atmosphere, in a microwave at 120° C. and 140 watts. Ethyl acetate was added to the reaction mixture and the whole was washed with H$_2$O, dried and concentrated. The crude product was reacted in step c without any further purification.

c) 4-[3-(2-chloro-4,5-difluorobenzoyl)ureido]-3-(2-methoxycarbonylvinyl)benzoic acid 4-Amino-3-(2-methoxycarbonylvinyl)benzoic acid was reacted with 2-chloro-4,5-difluorobenzoyl isocyanate, in analogy with example 2 b, to give the desired product.

M.p.: 216° C.

18

We claim:
1. A compound of the formula I,

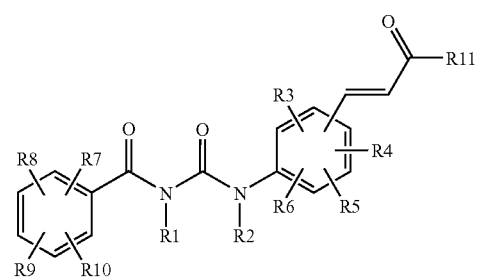

in which

R7, R8, R9 and R10 are, independently of each other, H, F, Cl, Br, OH, NO$_2$, CN, O—(C$_1$–C$_6$)-alkyl, O—(C$_2$–C$_6$)-alkenyl, O—(C$_2$–C$_6$)-alkynyl, O—SO$_2$—(C$_1$–C$_4$)-alkyl, (C$_1$–C$_6$)-alkyl, (C$_2$–C$_6$)-alkenyl or (C$_2$–C$_6$)-alkynyl, wherein the O—(C$_1$–C$_6$)-alkyl, O—(C$_2$–C$_6$)-alkenyl, O—(C$_2$–C$_6$)-alkynyl, O—SO$_2$—(C$_1$–C$_4$)-alkyl, (C$_1$–C$_6$)-alkyl, (C$_2$–C$_6$)-alkenyl and (C$_2$–C$_6$)-alkynyl groups can be substituted, more than once, by F, Cl or Br;

R1 and R2 are, independently of each other, H, O—(C$_1$–C$_6$)-alkyl, CO—(C$_1$–C$_6$)-alkyl, COO—(C$_1$–C$_6$)-alkyl, (C$_1$–C$_6$)-alkylene-COOH, (C$_1$–C$_6$)-alkylene-COO—(C$_1$–C$_6$)-alkyl or (C$_1$–C$_6$)-alkyl, wherein the (C$_1$–C$_6$)-alkyl group can be substituted by OH, O—(C$_1$–C$_4$)-alkyl, NH$_2$, NH(C$_1$–C$_4$)-alkyl or N[(C$_1$–C$_6$)-alkyl]$_2$;

R3, R4, R5 and R6 are, independently of each other, H, F, Cl, Br, NO$_2$, CN, O—R12, S—R12, COOR12, N(R13)(R14), N(R13)COR15, (C$_1$–C$_6$)-alkyl, (C$_2$–C$_6$)-alkenyl, (C$_2$–C$_6$)-alkynyl, (C$_3$–C$_7$)cycloalkyl or (C$_3$–C$_7$)-cycloalkyl-(C$_1$–C$_4$)-alkylene, wherein the (C$_1$–C$_6$)-alkyl, (C$_2$–C$_6$)-alkenyl, (C$_2$–C$_6$)-alkynyl, (C$_3$–C$_7$) cycloalkyl and (C$_3$–C$_7$)-cycloalkyl-(C$_1$–C$_4$)-alkylene groups can be substituted, more than once, by F, Cl, Br, OR12, COOR12 or N(R16)(R17);

R11 is OR12 or N(R18)(R19);

R12 is H, (C$_1$–C$_8$)-alkyl, (C$_2$–C$_8$)-alkenyl or (C$_2$–C$_8$)-alkynyl, wherein the (C$_1$–C$_8$)-alkyl, (C$_2$–C$_8$)-alkenyl and (C$_2$–C$_8$)-alkynyl groups can be substituted, more than once, by F, Cl, Br, OH or O(C$_1$–C$_4$)-alkyl;

R13 and R14 are, independently of each other, H, (C$_1$–C$_8$)-alkyl, (C$_2$–C$_8$)-alkenyl, (C$_2$–C$_8$)-alkynyl, (C$_3$–C$_7$)-cycloalkyl, (C$_3$–C$_7$)-cycloalkyl-(C$_1$–C$_4$)-alkylene, COO—(C$_1$–C$_4$)-alkyl, COO—(C$_2$–C$_4$)-alkenyl, phenyl or SO$_2$-phenyl, wherein the phenyl ring of the phenyl and SO$_2$-phenyl groups can be substituted, up to two times, by F, Br, Cl, CN, OH, (C$_1$–C$_6$)-alkyl, O—(C$_1$–C$_6$)-alkyl, CF$_3$, OCF$_3$, COOH, COO—(C$_1$–C$_6$)-alkyl or CONH$_2$;

or the radicals R13 and R14 form, with the nitrogen atom to which they are bonded, a 3-7-membered, saturated heterocyclic ring which can contain up to 2 further heteroatoms from the group N, O or S, wherein the heterocyclic ring can be substituted, up to three times, by F, Cl, Br, OH, Oxo, N(R20)(R21) or (C$_1$–C$_4$)-alkyl;

R16 and R17 are, independently of each other, H, (C$_1$–C$_8$)-alkyl, (C$_2$–C$_8$)-alkenyl, (C$_2$–C$_8$)-alkynyl, (C$_3$–C$_7$)-cycloalkyl, (C$_3$–C$_7$)-cycloalkyl-(C$_1$–C$_4$)-alkylene, COO—(C$_1$–C$_4$)-alkyl, COO—(C$_2$–C$_4$)-alkenyl, phenyl or $SO_2$-phenyl, wherein the phenyl ring of the phenyl and $SO_2$-phenyl groups can be substituted, up to two times, by F, Br, Cl, CN, OH, $(C_1-C_6)$-alkyl, O—$(C_1-C_6)$-alkyl, $CF_3$, $OCF_3$, COOH, COO—$(C_1-C_6)$-alkyl or $CONH_2$;

or the radicals R16 and R17 form, with the nitrogen atom to which they are bonded, a 3-7-membered, saturated heterocyclic ring which can contain up to 2 further heteroatoms from the group N, O or S, wherein the heterocyclic ring can be substituted, up to three times, by F, Cl, Br, OH, Oxo, N(R20)(R21) or $(C_1-C_4)$-alkyl;

R18, R19 are, independently of each other, H, $(C_1-C_8)$-alkyl, $(C_2-C_8)$-alkenyl, $(C_2-C_8)$-alkynyl, $(C_3-C_7)$-cycloalkyl, $(C_3-C_7)$-cycloalkyl-$(C_1-C_4)$-alkylene, COO—$(C_1-C_4)$-alkyl, COO—$(C_2-C_4)$-alkenyl, phenyl or $SO_2$-phenyl, wherein the phenyl ring of the phenyl and $SO_2$-phenyl groups can be substituted, up to two times, by F, Br, Cl, CN, OH, $(C_1-C_6)$-alkyl, O—$(C_1-C_6)$-alkyl, $CF_3$, $OCF_3$, COOH, COO—$(C_1-C_6)$-alkyl or $CONH_2$;

or the radicals R18 and R19, together with the nitrogen atom to which they are bonded, form a 3-7-membered, saturated heterocyclic ring which can contain up to 2 further heteroatoms from the group N, O or S, where the heterocyclic ring can be substituted, up to three times, by F, Cl, Br, OH, Oxo, N(R20)(R21) or $(C_1-C_4)$-alkyl;

R22 and R23 are, independently of each other, H, $(C_1-C_8)$-alkyl, $(C_2-C_8)$-alkenyl, $(C_2-C_8)$-alkynyl, $(C_3-C_7)$-cycloalkyl, $(C_3-C_7)$-cycloalkyl-$(C_1-C_4)$-alkylene, COO—$(C_1-C_4)$-alkyl, COO—$(C_2-C_4)$-alkenyl, phenyl or $SO_2$-phenyl, wherein the phenyl ring of the phenyl and $SO_2$-phenyl groups can be substituted up to two times, by F, Br, Cl, CN, OH, $(C_1-C_6)$-alkyl, O—$(C_1-C_6)$-alkyl, $CF_3$, $OCF_3$, COOH, COO—$(C_1-C_6)$-alkyl or $CONH_2$;

or the radicals R22 and R23, together with the nitrogen atom to which they are bonded, form a 3-7-membered, saturated heterocyclic ring which can contain up to 2 further heteroatoms from the group N, O or S, where the heterocyclic ring can be substituted, up to three times, by F, Cl, Br, OH, Oxo, N(R20)(R21) or $(C_1-C_4)$-alkyl;

R15 is $(C_1-C_8)$-alkyl, $(C_2-C_8)$-alkenyl, $(C_2-C_8)$-alkynyl, $(C_3-C_7)$-cycloalkyl, $(C_3-C_7)$-cycloalkyl-$(C_1-C_4)$-alkylene, wherein the $(C_1-C_8)$-alkyl, $(C_2-C_8)$-alkenyl, $(C_2-C_8)$-alkynyl, $(C_3-C_7)$-cycloalkyl and $(C_3-C_7)$-cycloalkyl-$(C_1-C_4)$-alkylene groups can be substituted more than once by F, $NH_2$, $NH(C_1-C_4)$-alkyl, $N[(C_1-C_4)$-alkyl]2, OH, O—$(C_1-C_4)$-alkyl, O—$(C_2-C_4)$-alkenyl) or O—CO—$(C_1-C_4)$-alkyl, COOR12, CON(R13)(R14), heteroaryl, $(C_6-C_{10})$-aryl or $(C_6-C_{10})$-aryl-$(C_1-C_4)$-alkylene, wherein the heteroaryl, $(C_6-C_{10})$-aryl and $(C_6-C_{10})$-aryl-$(C_1-C_4)$-alkylene groups can be substituted by O—$(C_1-C_4)$-alkyl, wherein the O—$(C_1-C_4)$-alkyl group can be substituted, more than once, by F, Br or Cl;

R20 and R21 are, independently of each other, H, $(C_1-C_8)$-alkyl, $(C_2-C_8)$-alkenyl, $(C_2-C_8)$-alkynyl, $(C_3-C_7)$-cycloalkyl, $(C_3-C_7)$-cycloalkyl-$(C_1-C_4)$-alkylene, COO—$(C_1-C_4)$-alkyl, COO—$(C_2-C_4)$-alkenyl, phenyl or $SO_2$-phenyl, wherein the phenyl ring of the phenyl and $SO_2$-phenyl groups can be substituted, up to two times, by F, Br, Cl, CN, OH, $(C_1-C_6)$-alkyl, O—$(C_1-C_6)$-alkyl, $CF_3$, $OCF_3$, COOH, COO—$(C_1-C_6)$-alkyl or $CONH_2$;

and pharmaceutically acceptable salts thereof.

2. The compound of claim 1 wherein

R7, R8, R9 and R10 are, independently of each other, H, F, Cl, Br, OH, $NO_2$, CN, O—$(C_1-C_6)$-alkyl, O—$(C_2-C_6)$-alkenyl, O—$(C_2-C_6)$-alkynyl, O—$SO_2$—$(C_1-C_4)$-alkyl, $(C_1-C_6)$-alkyl, $(C_2-C_6)$-alkenyl or $(C_2-C_6)$-alkynyl, wherein the O—$(C_1-C_6)$-alkyl, O—$(C_2-C_6)$-alkenyl, O—$(C_2-C_6)$-alkynyl, O—$SO_2$—$(C_1-C_4)$-alkyl, $(C_1-C_6)$-alkyl, $(C_2-C_6)$-alkenyl and $(C_2-C_6)$-alkynyl groups can be substituted, more than once, by F, Cl or Br;

R1 and R2 are H;

R3, R4, R5 and R6 are, independently of each other, H, F, Cl, Br, $NO_2$, CN, O—R12, S—R12, COOR12, N(R13)(R14), N(R13)COR15, $(C_1-C_6)$-alkyl, $(C_2-C_6)$-alkenyl, $(C_2-C_6)$-alkynyl, $(C_3-C_7)$-cycloalkyl or $(C_3-C_7)$-cycloalkyl-$(C_1-C_4)$-alkylene, wherein the $(C_1-C_6)$-alkyl, $(C_2-C_6)$-alkenyl, $(C_2-C_6)$-alkynyl, $(C_3-C_7)$-cycloalkyl and $(C_3-C_7)$-cycloalkyl-$(C_1-C_4)$-alkylene groups can be substituted, more than once, by F, Cl, Br, OR12, COOR12 or N(R16)(R17);

R11 is OR12 or N(R18)(R19);

R12 is H, $(C_1-C_8)$-alkyl, $(C_2-C_8)$-alkenyl or $(C_2-C_8)$-alkynyl, wherein the $(C_1-C_8)$-alkyl, $(C_2-C_8)$-alkenyl and $(C_2-C_8)$-alkynyl groups can be substituted, more than once, by F, Cl, Br, OH or O—$(C_1-C_4)$-alkyl;

R13 and R14 are, independently of each other, H, $(C_1-C_8)$-alkyl, $(C_2-C_8)$-alkenyl, $(C_2-C_8)$-alkynyl, $(C_3-C_7)$-cycloalkyl, $(C_3-C_7)$-cycloalkyl-$(C_1-C_4)$-alkylene, COO—$(C_1-C_4)$-alkyl, COO—$(C_2-C_4)$-alkenyl, phenyl or $SO_2$-phenyl, wherein the phenyl ring of the phenyl and $SO_2$-phenyl groups can be substituted, up to two times, by F, Br, Cl, CN, OH, $(C_1-C_6)$-alkyl, O—$(C_1-C_6)$-alkyl, $CF_3$, $OCF_3$, COOH, COO—$(C_1-C_6)$-alkyl or $CONH_2$;

or the radicals R13 and R14 form, with the nitrogen atom to which they are bonded, a 3-7-membered, saturated heterocyclic ring which can contain up to 2 further heteroatoms from the group N, O or S, wherein the heterocyclic ring can be substituted, up to three times, by F, Cl, Br, OH, Oxo, N(R20)(R21) or $(C_1-C_4)$-alkyl;

R16 and R17 are, independently of each other, H, $(C_1-C_8)$-alkyl, $(C_2-C_8)$-alkenyl, $(C_2-C_8)$-alkynyl, $(C_3-C_7)$-cycloalkyl, $(C_3-C_7)$-cycloalkyl-$(C_1-C_4)$-alkylene, COO—$(C_1-C_4)$-alkyl, COO—$(C_2-C_4)$-alkenyl, phenyl or $SO_2$-phenyl, wherein the phenyl ring of the phenyl and $SO_2$-phenyl groups can be substituted, up to two times, by F, Br, Cl, CN, OH, $(C_1-C_6)$-alkyl, O—$(C_1-C_6)$-alkyl, $CF_3$, $OCF_3$, COOH, COO—$(C_1-C_6)$-alkyl or $CONH_2$;

or the radicals R16 and R17, together with the nitrogen atom to which they are bonded, form a 3-7-membered, saturated heterocyclic ring which can contain up to 2 further heteroatoms from the group N, O or S, wherein the heterocyclic ring can be substituted, up to three times, by F, Cl, Br, OH, Oxo, N(R20)(R21) or $(C_1-C_4)$-alkyl;

R18 and R19 are, independently of each other, H, $(C_1-C_8)$-alkyl, $(C_2-C_8)$-alkenyl, $(C_2-C_8)$-alkynyl, $(C_3-C_7)$-cycloalkyl, $(C_3-C_7)$-cycloalkyl-$(C_1-C_4)$-alkylene, COO—$(C_1-C_4)$-alkyl, COO—$(C_2-C_4)$-alkenyl, phenyl or $SO_2$-phenyl, wherein the phenyl ring of the phenyl and $SO_2$-phenyl groups can be substituted, up to two times, by F, Br, Cl, CN, OH, $(C_1-C_6)$-alkyl, O—$(C_1-C_6)$-alkyl, $CF_3$, $OCF_3$, COOH, COO—$(C_1-C_6)$-alkyl or $CONH_2$;

or the radicals R18 and R19, together with the nitrogen atom to which they are bonded, form a 3-7-membered, saturated heterocyclic ring which can contain up to 2 further heteroatoms from the group N, O or S, wherein the heterocyclic ring can be substituted, up to three times, by F, Cl, Br, OH, Oxo, N(R20)(R21) or $(C_1-C_4)$-alkyl;

R22 and R23 are, independently of each other, H, $(C_1-C_8)$-alkyl, $(C_2-C_8)$-alkenyl, $(C_2-C_8)$-alkynyl, $(C_3-C_7)$-cycloalkyl, $(C_3-C_7)$-cycloalkyl-$(C_1-C_4)$-alkylene, COO—$(C_1-C_4)$-alkyl, COO—$(C_2-C_4)$-alkenyl, phenyl or $SO_2$-phenyl, wherein the phenyl ring of the phenyl and $SO_2$-phenyl groups can be substituted, up to two times, by F, Br, Cl, CN, OH, $(C_1-C_6)$-alkyl, O—$(C_1-C_6)$-alkyl, $CF_3$, $OCF_3$, COOH, COO—$(C_1-C_6)$-alkyl or $CONH_2$;

or the radicals R22 and R23, together with the nitrogen atom to which they are bonded, form a 3-7-membered, saturated heterocyclic ring which can contain up to 2 further heteroatoms from the group N, O or S, wherein the heterocyclic ring can be substituted, up to three times, by F, Cl, Br, OH, Oxo, N(R20)(R21) or $(C_1-C_4)$-alkyl;

R15 is $(C_1-C_8)$-alkyl, $(C_2-C_8)$-alkenyl, $(C_2-C_8)$-alkynyl, $(C_3-C_7)$-cycloalkyl or $(C_3-C_7)$-cycloalkyl-$(C_1-C_4)$-alkylene, wherein the $(C_1-C_8)$-alkyl, $(C_2-C_8)$-alkenyl, $(C_2-C_8)$-alkynyl, $(C_3-C_7)$-cycloalkyl and $(C_3-C_7)$-cycloalkyl-$(C_1-C_4)$-alkylene groups can be substituted more than once by F, $NH_2$, $NH(C_1-C_4)$-alkyl, $N[(C_1-C_4)$-alkyl$]_2$, OH, O—$(C_1-C_4)$-alkyl, O—$(C_2-C_4)$-alkenyl) or O—$CO(C_1-C_4)$-alkyl, COOR12, CON(R13)(R14), heteroaryl, $(C_6-C_{10})$aryl, $(C_6-C_{10})$-aryl-$(C_1-C_4)$-alkylene, wherein the heteroaryl, $(C_6-C_{10})$-aryl and $(C_6-C_{10})$-aryl-$(C_1-C_4)$-alkylene groups can be substituted by O—$(C_1-C_4)$-alkyl, wherein the O—$(C_1-C_4)$-alkyl group can be substituted, more than once, by F, Br or Cl;

R20 and R21 are, independently of each other, H, $(C_1-C_8)$-alkyl, $(C_2-C_8)$-alkenyl, $(C_2-C_8)$-alkynyl, $(C_3-C_7)$-cycloalkyl, $(C_3-C_7)$-cycloalkyl-$(C_1-C_4)$-alkylene, COO—$(C_1-C_4)$-alkyl, COO—$(C_2-C_4)$-alkenyl, phenyl or $SO_2$-phenyl, wherein the phenyl ring of the phenyl and $SO_2$-phenyl groups can be substituted, up to two times, by F, Br, Cl, CN, OH, $(C_1-C_6)$-alkyl, O—$(C_1-C_6)$-alkyl, $CF_3$, $OCF_3$, COOH, COO—$(C_1-C_6)$-alkyl or $CONH_2$;

and pharmaceutically acceptable salts thereof.

3. The compound of claim 2 wherein:
R7, R8, R9 and R10 are, independently of each other, H, F or Cl;
R1, R2 and R6 are H;
R3, R4, R5 and R6 are, independently of each other, H, Cl, COOH, COO—$(C_1-C_4)$-alkyl or NHCOR15;
R11 is OR12 or N(R18)(R19);
R12 is H or $(C_1-C_4)$-alkyl;
R18, R19 are, independently of each other, H or $(C_1-C_4)$-alkyl;
R15 is $(C_1-C_4)$-alkyl, wherein alkyl can be substituted by COOH;

and pharmaceutically acceptable salts thereof.

4. A pharmaceutical composition comprising a pharmaceutically acceptable carrier and one or more compounds of claim 1.

5. A pharmaceutical composition comprising a pharmaceutically acceptable carrier, one or more compounds of claim 1 and one or more blood sugar-lowering active compounds.

6. A method of treating type 2 diabetes comprising administering to a patient in need thereof a therapeutically effective amount of a compound of claim 1.

7. A method of lowering blood sugar comprising administering to a patient in need thereof a therapeutically effective amount of a compound of claim 1.

8. A method of treating type 2 diabetes comprising administering to a patient in need thereof a therapeutically effective amount of a compound of claim 1 in combination with at least one further blood sugar-lowering active compound.

9. A method of lowering blood sugar comprising administering to a patient in need thereof a therapeutically effective amount of a compound of claim 1 in combination with at least one further blood sugar-lowering active compound.

10. A process for producing a pharmaceutical composition comprising one or more compounds of claim 1, which comprises mixing the compound of claim 1 with a pharmaceutically suitable excipient and bringing this mixture into a form which is suitable for administration.

* * * * *